(12) United States Patent
Appenzeller et al.

(10) Patent No.: US 8,915,924 B2
(45) Date of Patent: Dec. 23, 2014

(54) DRILL GUIDE SYSTEM

(75) Inventors: Andreas Appenzeller, Langendorf (CH); Ladislav Nagy, Kirchberg (CH); Andreas Schweizer, Zurich (CH); Daniel Fluri, Langendorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 976 days.

(21) Appl. No.: 12/915,614

(22) Filed: Oct. 29, 2010

(65) Prior Publication Data

US 2011/0144647 A1 Jun. 16, 2011

Related U.S. Application Data

(60) Provisional application No. 61/285,755, filed on Dec. 11, 2009.

(51) Int. Cl.
*A61B 17/60* (2006.01)
*A61F 2/00* (2006.01)
*A61B 17/17* (2006.01)

(52) U.S. Cl.
CPC ..... *A61B 17/1728* (2013.01); *A61B 2017/1782* (2013.01); *A61B 17/1732* (2013.01)
USPC .......................................................... 606/96

(58) Field of Classification Search
USPC .............................. 606/96–98, 280, 281, 286
See application file for complete search history.

(56) References Cited

U.S. PATENT DOCUMENTS

| 6,007,535 | A | 12/1999 | Rayhack et al. | |
|---|---|---|---|---|
| 7,367,977 | B2 * | 5/2008 | Estrada, Jr. ..................... | 606/54 |
| 2005/0154394 | A1 | 7/2005 | Michalowicz | |
| 2006/0089648 | A1 | 4/2006 | Masini | |
| 2009/0254126 | A1 | 10/2009 | Orbay et al. | |

FOREIGN PATENT DOCUMENTS

EP 0995403 4/2000
WO WO 2004/045389 6/2004

OTHER PUBLICATIONS

U.S. Appl. No. 12/770,088, filed Apr. 29, 2010, Furrer et al.
U.S. Appl. No. 12/851,964, filed Aug. 6, 2010, Regazzoni.

\* cited by examiner

*Primary Examiner* — Anu Ramana
(74) *Attorney, Agent, or Firm* — Baker & Hostetler LLP

(57) ABSTRACT

A drill guide includes a first bone plate that extends along a first middle plane, and a second bone plate that extends along a second middle plane. The drill guide further includes a first articulation and a second articulation that is connected to the first articulation. The first and second articulations are arranged between the first and the second bone plate. Each of the first and second articulations is releasably lockable.

24 Claims, 7 Drawing Sheets

DRILL GUIDE SYSTEM

CROSS-REFERENCE TO RELATED APPLICATIONS

This claims priority to U.S. Provisional Patent Application Ser. No. 61/285,755 filed Dec. 11, 2009, the disclosure of which is hereby incorporated by reference as if set forth in its entirety herein.

FIELD OF THE DISCLOSURE

The present disclosure generally relates to bone fixation, and in particular relates to a drill guide system for post-osteotomy bone plates.

BACKGROUND

Unreduced bone fractures and malunited fractures can cause considerable loss of anatomical function. For instance, an unreduced radial head in a malunited fracture can cause considerable loss of anatomical forearm function. Unreduced and malunited extraarticular fractures of the distal radius can be subsequently treated with a planned corrective osteotomy. Correct preoperative planning of the corrective osteotomy can be achieved on the bases of two-dimensional X-ray image data or three-dimensional Computer Tomography data. One such system related to an osteotomy of a maxilla is disclosed in U.S. patent application Ser. No. 12/770,088 filed on Apr. 29, 2010, the disclosure of which is hereby incorporated by reference as if set forth in its entirety herein. While extraarticular bone fixation plates can be used to fix the bone segments achieved post-osteotomy, it is desired to provide a method and apparatus for providing a preoperative planned correction.

SUMMARY

In accordance with one embodiment, a method and apparatus are provided that provide a pre-operatively selected cutting line to realign fractured bones (e.g., of the distal radius) that may have been joined in an incorrect non-anatomical way. Correction of the mal-alignment involves cutting bone at a desired place so as to divide the bone into a pair of bone segments, re-positioning the bone segments in a longitudinal and rotational correct position, and fixing the bone segments in the correct position so that they can be re-united correctly. The fixation can be effected with any suitably constructed bone plate, such as a T-shaped bone plate or an L-shaped bone plate in a right or left side configuration.

According to the inventive solution of the above object a pre-operative planning is performed in which the corrections between the two bone segments, in particular the rotational corrections and the longitudinal axial correction are determined before performing the cutting of the mal-united bone.

In accordance with one aspect, a drill guide for a distal radius plate is provided which comprises a first longitudinal bone plate substantially defining a first middle plane, a second transverse bone plate substantially defining a second middle plane, a first articulation and a second articulation connected to the first articulation. The first and second articulations are arranged between the first and the second bone plate and each of the first and second articulations is releasably lockable.

The drill guide allows the bone fixation holes for the bone anchors that secure the bone fixation plate to the bone segments can be drilled prior to performing the corrective osteotomy. The drill guide can be adjusted to position the transverse bone plate relative to the longitudinal bone plate in such manner that once the osteotomy has been performed the plate holes of a T-shaped bone plate coincide with the bone fixation holes drilled before performing the pre-operatively planned osteotomy.

The correction values of the drill guide can be adjusted directly using small scales on the drill guide. Alternatively or additionally, an auxiliary device is configured to adjust the correction values of the drill guide using larger scales of the auxiliary device so as to enhance visibility of the scales.

According to another embodiment the first articulation comprises a first axis of rotation and the second articulation comprises a second axis of rotation which is not parallel to the first axis of rotation. The first and second axis of rotation are skewed, or angularly offset, relative to each other. The first and second articulation can be configured so as to not define a spherical joint.

According to a further embodiment one of the first and second axis of rotation is substantially perpendicular to the first middle plane.

In yet another embodiment the other one of the first and second axis of rotation lies substantially in the second middle plane.

In a further embodiment of the drill guide the first and second articulation are configured as releasably lockable ball-and-socket joints and wherein the first and second articulation comprise a first, respectively second axis of rotation. Accordingly, the first and second bone plates can be rotated relative to each other with respect to three degrees of freedom.

In a further embodiment of the drill guide one of the first and second axis of rotation lies substantially in the first middle plane.

In again a further embodiment of the drill guide the other one of the first and second axis of rotation lies substantially in the second middle plane.

In another embodiment of the drill guide, the first articulation is coupled to the first bone plate and the second articulation is coupled to the second bone plate, and an arm comprising a first and a second arm portion is coupled between the first and second articulation, wherein the first and second arm portion are pivotally coupled to each other by a central articulation, which can be provided as a hinge joint. Accordingly, the first and second bone plate can be moved relative to each other with respect to six degrees of freedom.

In another embodiment of the drill guide the first bone plate comprises a first and a second lateral extension each comprising a housing with a socket of one of the ball-and-socket joints and wherein the first and second lateral extension measured in the first middle plane can be equidistantly spaced from the longitudinal axis of the first bone plate. Accordingly, the drill guide can be used to align both the left radius and the right radius of a patient.

In again another embodiment of the drill guide the first and second arm portion each comprises a ball of one of the ball-and-socket joints and wherein each ball is located at an end of each of the first and second arm portion opposite the central articulation.

According to again another embodiment the second bone plate is arranged transverse at an angle α to the first bone plate.

According to a further embodiment the angle α is adjustable by pivoting the second bone plate about the first axis of rotation, respectively about the first and/or second axis of rotation. The angle α between the longitudinal axis of the first bone plate and the longitudinal axis of the second bone plate measured in a plane parallel to the first middle plane can be in a range having a lower end of approximately 50°, and alternatively approximately 55°, and an upper end of approximately 130°, and alternatively approximately 125°. In accordance with one embodiment the angle α is approximately 50°. This first correction angle α corresponds to the rotation of the osteotomied joint head about an axis of rotation extending in the dorsal-palmar direction of the radius.

According to another embodiment the first bone plate comprises a longitudinal axis and the first axis of rotation. The first axis of rotation is located at a non-zero distance from the central longitudinal axis of the first bone plate between approximately 15 mm and 20 mm, such as approximately 18 mm. Accordingly, the transverse bone plate can be displaced relative to the longitudinal portion in a direction that can have one or both of a rotation component and a translation component so as to simulate a pivot axis extending in the dorsal-palmar direction of the radius defined by the osteotomy. The distance A can be selected so that rotation of the distal radius head can be effected after the osteotomy has been performed in a plane orthogonal to the dorsal-palmar direction of the radius. The rotation of the distal radius head can be performed about an axis of rotation defined by the tip of the osteotomy cut.

According to a further embodiment the second bone plate comprises at least two plate holes each having the form of a key-hole which comprises an enlarged portion allowing a screw head of a bone anchor to pass therethrough.

According to yet another embodiment the second bone plate comprises at least two plate holes having a channel extending from the respective plate hole towards the periphery of the second bone plate allowing to remove the second plate from two or more bone anchors in a direction parallel to the second middle plane. Two or all of the plate holes in the second bone plate can be configured with a channel extending in a distal direction from the plate hole to the periphery of the second bone plate. If the channels of the plate holes in the second bone plate extend in a lateral direction from the plate hole to the periphery of the second bone plate the channels extend in opposite lateral directions from the outer two plate holes towards the periphery of the second bone plate. The channels between the plate holes and the periphery of the second bone plate allow the bone anchors to remain fixed to the underlying bone, but can be loosened so that the bone fixation plate can be translated such that the bone anchors pass through the channels.

According to a further embodiment the first bone plate comprises scale that extends parallel to the central longitudinal axis of the first bone plate, and defines a marked zero-position. The scale allows a drill bit to be positioned at a predetermined distance from the zero-position corresponding to a pre-operatively planned length of correction of the osteotomy.

In another embodiment of the drill guide the second bone plate comprises two through channels which are open towards the periphery of the second bone plate. Accordingly, the second bone plate can be positioned on an auxiliary device in a defined position.

In another embodiment of the drill guide the second bone plate comprises two or more through holes configured to receive a guide wire each. The drill guide can thus be fixed to by the guide wires.

The first bone plate can include a pair of elongated plate holes, wherein each of the elongated plate holes comprises a first section with a conical thread and a second section with a recess which enlarges, for instance spherically, towards the top surface of the first bone plate. The second bone plate can comprise four plate holes arranged on a longitudinal axis of the second bone plate and each being provided with a conical thread. Furthermore, the first and second articulations can be releasably lockable using respective locking screws that fix the first and second articulations a desired position. The drill guide can be made from any suitable material, such as stainless steel and alloys thereof, titanium and titanium alloys or PEEK.

The embodiments of the drill guide for the right hand side and left hand side differ only therein that the first articulation is arranged at a distance A measured in the right or left direction from the longitudinal axis of the first bone plate.

In accordance with a further aspect, an auxiliary device for the drill guide is provided. The auxiliary device comprises a base plate that defines a central axis of rotation, a rotatable member rotatably arranged on the base plate in such a manner that the rotatable member is rotatable about the central axis of rotation, a first positioning member arranged on the base plate and including a seat configured to receive the first bone plate and a second positioning member fixed on the rotatable member. The second positioning member includes a slideable member and is configured to angularly adjust the second bone plate.

The slideable member can be slideably displaceable on an arc in such manner that the second middle plane of the second bone plate is located at an angle β of minimum 0° with respect to the first middle plane of the first bone plate. The angle β is maximum ±60°. The angle β allows a rotation of the second bone plate about an axis which is orthogonal to the dorsal-palmar direction of the radius and orthogonal or oblique to the longitudinal axis of the radius. The zero position of the plane surface of the slideable member is defined so that the second middle plane of the second bone plate is at an angle of +25° with respect to the first middle plane of the first bone plate. Typically the second bone plate is rotated about the second axis of rotation, respectively the second and/or first axis of rotation with an angle in a range between −50° and +40° (for an application for the tibia up to 90°) with respect to the zero position. The first positioning member can include a first fastener to releasably fix the first bone plate in the seat. The slideable member can comprise a second fastener to releasably fix the second bone plate to the second positioning member. Furthermore, the rotatable member can be releasably fixable with respect to the base plate.

In a further embodiment of the auxiliary device the first positioning member is fixedly arranged on the base plate and the seat defines an adjustment plane orthogonal to the central axis configured to receive the first bone plate in a position with the first middle plane parallel to the adjustment plane and the slideable member is slideable on an arc orthogonal to the adjustment plane. The seat is configured to receive the first bone plate with the first axis of rotation coinciding with the central axis of the base plate. Furthermore, the arc has a radius R with a center lying on the second axis of rotation when the first bone plate is mounted in the seat.

In another embodiment of the auxiliary device the first positioning member comprises a hinge joint with an axis of rotation orthogonal to the central axis.

In another embodiment of the auxiliary device the first positioning member is displaceable along an axis which can be substantially orthogonal to the central axis and can further be substantially orthogonal to the axis of rotation.

According to a further embodiment the seat of the first positioning member is configured to receive the first bone plate in a right side or in a left side embodiment.

According to another embodiment the first positioning member includes a first and a second seat configured to receive the first bone plate in a right side or in a left side embodiment.

In yet another embodiment of the auxiliary device the second positioning member comprises two or more positioning elements allowing to position the second bone plate of the drill guide in a defined position.

The drill guide can be further used to reduce fractures in the epiphysis of a long bone.

In accordance with a further aspect the method for performing a corrective operation of malunited extraarticular bone fractures comprises the following steps:

a) pre-operatively planning of angular and length correction values including selecting an osteotomy line to be performed and selecting a suitable bone plate for fixing the distal long bone osteotomy;

b) adjusting a drill guide using the angular corrections values established under step a);

c) marking the end position of the longitudinal portion of the bone plate to be used on the bone shaft segment;

d) positioning the drill guide with the guiding mark at the free end of the longitudinal portion of the adjusted drill guide at the marked position on the bone shaft segment and holding the longitudinal portion there manually or using an instrument;

e) drilling the bone fixation holes through the bone fixation holes of the transverse portion of the drill guide into the distal bone segment;

f) drilling one or more bone fixation holes in the shaft segment, while applying the pre-planned longitudinal correction by positioning the holes at a desired longitudinally corrective location on the scale that is located adjacent to the elongated hole of the drill guide. The longitudinal correction is applied by positioning the tip of the drill bit at a distance from the marked zero-position measured on the scale which coincides with the longitudinal correction of the osteotomy determined under step a);

g) removing the drill guide;

h) performing the pre-planned osteotomy;

i) fixing the pre-selected bone plate with bone anchors at the transverse portion to the distal segment;

j) reducing the bone segments angularly and axially so that a bone anchor can be set through the longitudinal portion of the bone plate into the pre-drill bone hole in the shaft segment; and k) setting one or more additional bone anchors through the longitudinal portion of the bone plate according to the length correction value determined under step a).

In accordance with one embodiment, the angular and length correction values include rotation angles of an osteotomied epiphyseal bone portion relative to a remaining long bone portion and a displacement length of the osteotomied epiphyseal bone portion relative to the remaining long bone portion.

According to a further embodiment the step of drilling the bone fixation holes through the transverse portion of the drill guide and the step of removing the drill guide are composed by the steps of:

e1) drilling the bone fixation holes through the bone fixation holes of the transverse portion of the drill guide into the distal bone segment;

e2) fixing the drill guide with bone anchors at the transverse portion to the distal segment;

g1) loosening the bone anchors at the transverse portion of the drill guide; and g2) removing the drill guide by displacing the transverse portion in such manner that the screw heads of the bone anchors pass through the enlarged portion of the key-hole shaped plate holes or that the bone anchors pass through the open plate holes towards the periphery of the transverse portion.

Bone chips can be introduced into the osteotomy gap produced between the two correctly repositioned bone segments to further facilitate healing.

In accordance with again another aspect a kit for drilling bone fixation holes in bone segments in a pre-operatively planned position is provided including the drill guide the auxiliary device.

In accordance with yet another aspect a kit for performing and fixing of a corrective osteotomy is provided including the drill guide and a bone plate, such as a T-shaped bone plate or an L-shaped bone plate in a right side or in a left side configuration.

DESCRIPTION OF THE DRAWINGS

The foregoing summary, as well as the following detailed description of preferred embodiments of the application, will be better understood when read in conjunction with the appended drawings. For the purposes of illustrating the embodiments of the present application, there is shown in the drawings certain embodiments. It should be understood, however, that the application is not limited to the precise arrangements and instrumentalities shown. In the drawings.

DETAILED DESCRIPTION

Figure 1:
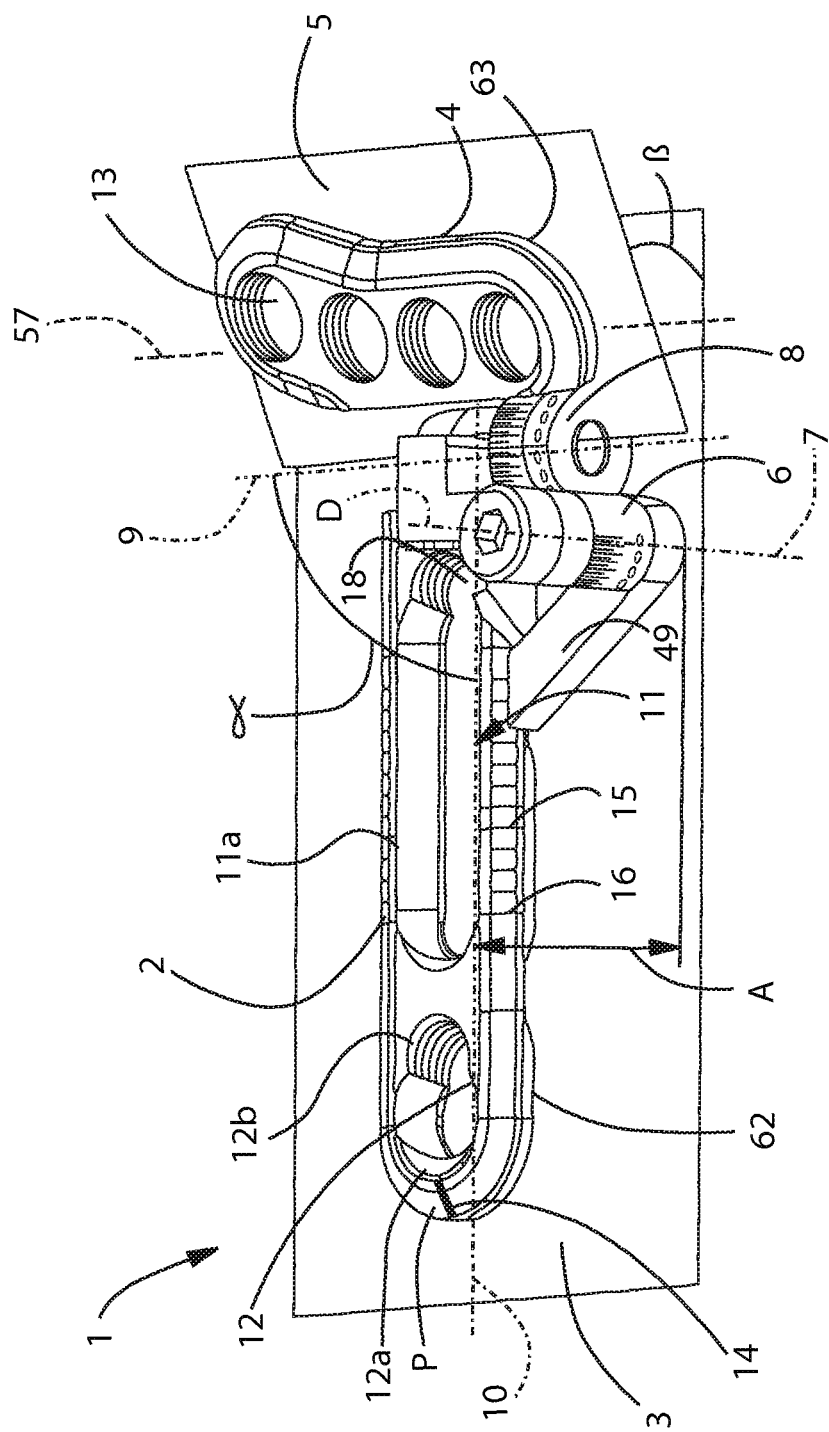
FIG. 1 is a perspective view of a drill guide constructed in accordance with one embodiment.

Referring to FIG. 1, a drill guide 1 allows bone plate fixation holes to be drilled into the underlying bone at predetermined locations prior to performing an osteotomy on the underlying bone. The bone fixation holes receive respective bone anchors that fix a pre-selected bone plate to the underlying bone segments at a predetermined location that aligns the bone segments in a predetermined position after the osteotomy has been performed. The underlying bone can be a distal radius, such that one plate of the drill guide can be placed over the radius shaft, and a second plate of the drill guide can be placed over the radius head, so as to reduce the osteotomy fracture of the distal radius in such a manner that the radius shaft and radius head are aligned as desired. It will become apparent that the drill guide can be used to align bone fixation holes in the epiphysis of any long bone as desired. The drill guide can be made from any suitable material, such as stainless steel and alloys thereof, titanium and titanium alloys or PEEK.

The drill guide 1 includes a first bone plate 2, a second bone plate 4 that is angularly offset with respect to the first bone plate 2, a first articulation 6 fixedly connected to the first bone plate 2 and a second articulation 8 located between the first articulation 6 and the second bone plate 4. As will be appreciated from the description below, the second bone plate 4 is rotatably relative to the first bone plate 2 about the first and second articulations 6 and 8, respectively. The first bone plate 2 is elongate along a central longitudinal axis 10, and defines a proximal end P and an opposed distal end D that is spaced from the proximal end P along the longitudinal axis 10. The first bone plate 2 further defines a bone contacting surface 62 that extends generally along a first middle plane 3 that extends along a bone-facing surface of the first bone plate 2. The second bone plate 4 extends along a respective long axis 57, and defines a bone-facing surface 63 that extends generally along a second middle plane 5. Each of the first and second articulations 6 and 8, respectively, cane be configured as a hinge and is releasably lockable using any suitable fastener as desired, such as a set screw, a grub screw, a standard screw, a stardrive screw, a socket, or any alternative fastener that an operator can fasten with a tool as would be understood by the skilled person. The first articulation 6 is configured to rotate about a first center of rotation, illustrated as a first axis of rotation 7, that extends substantially orthogonal to the first middle plane 3, i.e. in the dorsal-palmar direction of the distal radius. The second articulation 8 is configured to rotate about a second center of rotation, illustrated as a second axis of rotation 9. The first and second axes 7 and 9, respectively, are angularly offset (e.g., skewed) relative to each other. For instance, the second axis of rotation 9 can be substantially orthogonal with respect to the first axis of rotation 7. It should be appreciated that "orthogonal" components described herein can alternatively be angularly offset as desired. The first and second articulations 6 and 8 can provide non-spherical joints if desired.

The second axis of rotation 9 can lie in the second middle plane 5 and can extend along a direction transverse to the longitudinal axis of the distal radius in accordance with the illustrated embodiment. Thus, it can be said that one of the first and second axes of rotation 7 and 9 can be substantially perpendicular to the first middle plane 3, and the other of the first and second axes of rotation can lie substantially in the second middle plane 5. Each of the first and second bone plates 2 and 4, respectively, can define an elongated shape. The second bone plate 4 can be oriented so as to define a central long axis 57 positioned angularly offset or substantially orthogonal to the longitudinal axis 10 of the first bone plate 2. The elongated second bone plate 4 can define an angle relative to the long axis 57, but the second bone plate 4 can nevertheless be described as extending along the long axis 57. The second bone plate 4 further includes a first portion that is fixed at the second articulation 8 and extends parallel to the second axis of rotation 9. The second bone plate 4 includes a second portion opposite the first portion that extends at an angle relative to the second axis of rotation 9.

The second bone plate 4 can be rotated about the first axis of rotation 7 so as to adjust a first angle α to a pre-planned correction value. The angle α is defined by the longitudinal axis 10 of the first bone plate 2 and the second axis of rotation 9 of the second articulation 8 measured in a plane parallel to the first middle plane 3. Because the second axis of rotation 9 is substantially parallel to the long axis 57 of the second bone plate 4, the angle α can further be defined by the longitudinal axis of the first bone plate 2 and the long axis 57 of the second bone plate 4. Accordingly, the longitudinal axis of second bone plate 4 can be oriented angularly offset with respect to the longitudinal axis of the first bone plate 2 at the angle α that has been adjusted to the preplanned first correction angle. The angle α can define a minimum value of at least 50°, such as 55°, and a maximum value of at least 125°, such as 130°. Thus, the angle α can be within the range including and between approximately 50° and approximately 130°. The first correction angle α corresponds to the rotation of the osteotomied joint head about an axis of rotation extending in the dorsal-palmar direction of the distal radius.

The second bone plate 4 can be rotated about the second axis of rotation 9 so as to adjust a second angle β to a pre-planned correction angle. The angle β is defined by the second middle plane 5 and the first middle plane 3. It should be appreciated that a bone plate 50 (see FIG. 7) can be selected sized and shaped so as to correspond to the first and second pre-planned correction angles of the first and second angles α and β. The first articulation 6 is supported by an oblique extension 49 that protrudes out from first bone plate 2 such that the first axis of rotation 7 is spaced from the longitudinal axis 10 at a distance A that can be greater than half of the width of the first bone plate 2. The drill guide 1 can be selectively positioned in a right hand side configuration or a left hand configuration. In the right hand configuration, the first articulation 6 is positioned such that the first axis of rotation 7 is arranged in the right direction from the longitudinal axis 10. In the left hand configuration, the first articulation 6 is positioned such that the first axis of rotation 7 is arranged in the left direction from the longitudinal axis 10. Thus, the extension 49 can be fastened to either the right or the left side of the first bone plate 2.

The distance A between the axis of rotation 7 and the longitudinal axis 10 can be between approximately 15 mm and approximately 20 mm, such as approximately 18 mm. Because the axis of rotation 7 is spaced from the longitudinal axis 10, it should be appreciated that the second bone plate 4 can be displaced relative to the first bone plate 2 in a direction has both a rotation component and a translation component so as to simulate a pivot axis extending in the dorsal-palmar direction of the radius defined by the osteotomy. The distance A can be selected so that rotation of the distal radius head can be effected after the osteotomy has been performed in a plane orthogonal to the dorsal-palmar direction of the radius. The rotation of the distal radius head can be performed about an axis of rotation defined by the tip of the osteotomy cut.

The first bone plate 2 defines a first elongated plate hole 11 that extends therethrough. The plate hole 11 includes a longitudinally elongate slot 11a and a circular plate hole 18 disposed distal of the longitudinally elongate slot 11a such that the circular plate hole 18 defines an arc that extends greater than 180°. The circular plate hole 18 can include a conical internal thread to receive an angularly stable bone anchor (not shown) with a complementarily conically threaded screw head. Alternatively, the plate hole 18 can define a substantially smooth interior surface, or can include a portion that is smooth and a portion that is threaded. The longitudinally elongate slot 11a can enlarge, for instance substantially spherically, along a direction from the bone-facing surface 62 of the first bone plate 2 to the opposed top surface of the first bone plate 2. Thus, the first elongated plate hole 11 can include a first section with a conical thread and a second section with a recess which enlarges, for instance substantially spherically, towards the top surface of the first bone plate.

A second elongated plate hole 12 is spaced proximal from the first elongated plate hole 11. The second elongated plate hole 12 includes a combination of a pair of plate holes 12a and 12b. The plate hole 12b is distal with respect to the plate hole 12a, and the distal plate hole 12b defines a smaller than the proximal plate hole 12a. The distal plate hole 12b is provided with a conical interior thread, while the proximal plate hole 12a can define a substantially smooth interior. Alternatively, either or both of the plate holes 12a and 12b can be threaded, smooth, or have a first portion that is threaded and a second portion that is smooth. The circular plate holes 12a and 12b of the second plate hole 12 penetrate each other along the longitudinal axis 10 in such manner that each of the two plate holes 12a and 12b forms respective joined arcs, each arc extending greater than 180°.

The second bone plate 4 defines a plurality of (e.g., at least two) plate holes 13, such as four plate holes 13, that are substantially arranged along the long axis 57 of the second bone plate 4. Each of the plate holes 13 can include a conical internal thread to receive the screw head of an angularly stable bone anchor, or can be smooth or partially threaded and partially smooth as desired.

The first bone plate 2 further includes a scale 15 that extends in a direction substantially parallel to the longitudinal axis 10 at a location adjacent to the elongated plate hole 11. The scale 15 defines a marked zero-position 16. When drilling a bone fixation hole into an underlying bone, the drill bit can be positioned at a predetermined distance from the zero-position along the longitudinal axis 10 that corresponds to a pre-operatively planned corrective length dimension of the osteotomy. Further, a guiding mark 14 is arranged at the proximal end P (e.g., free end) of the first bone plate 2. The drill guide 1 can be positioned on an underlying bone such that the guiding mark 14 is aligned with a previously marked position on the radius shaft 61, as described below with reference to FIGS. 6-9, to ensure that the drill guide 1 is properly positioned on the underlying bone. Each of the first and second articulations 6 and 8 can also be provided with an angular degree scale as desired. Alternatively or additionally, the angular adjustments of the articulations 6 and 8 can be measured using respective scales of an auxiliary device 20 as shown in FIG. 5.

Figures 2, 3:
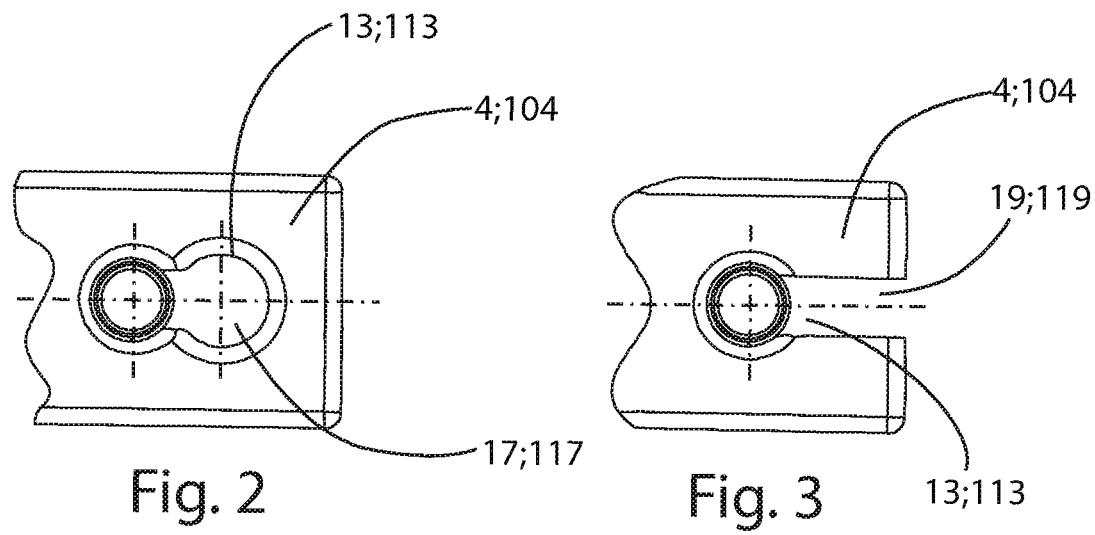
FIG. 2 is a top plan view of a portion of a drill guide similar to the drill guide illustrated in FIG. 1, but showing a key-shaped plate hole in accordance with another embodiment.
FIG. 3 is a top plan view of a portion of a drill guide similar to the drill guide illustrated in FIG. 1, but showing a plate hole which is open towards the periphery of the second bone plate in accordance with another embodiment.
Figure 4:
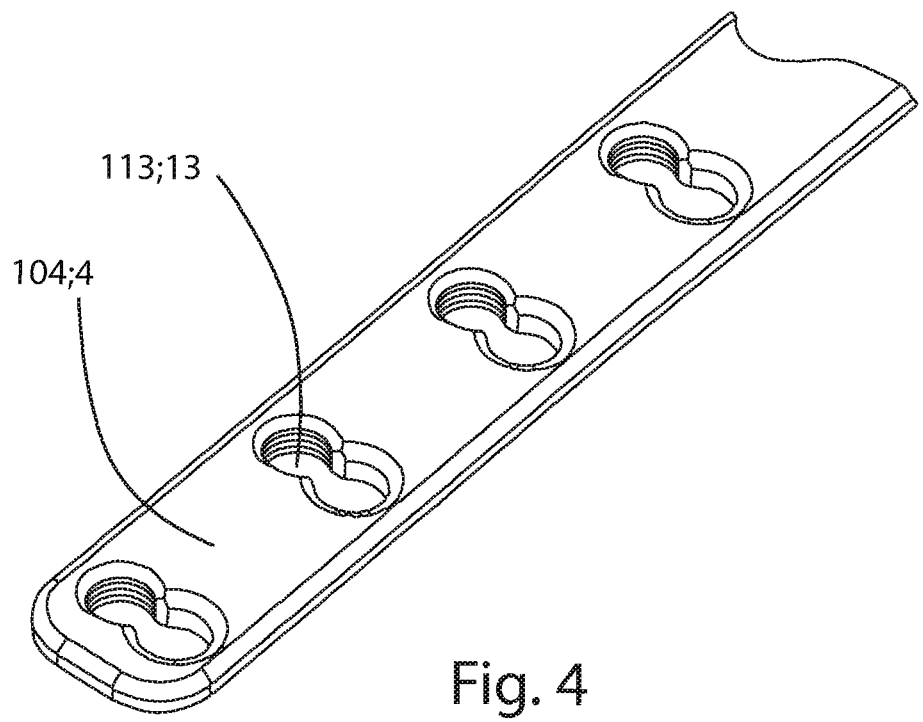
FIG. 4 is a perspective view of a portion of the second bone plate including key-shaped plate holes as illustrated in FIG. 2.
Figure 10:
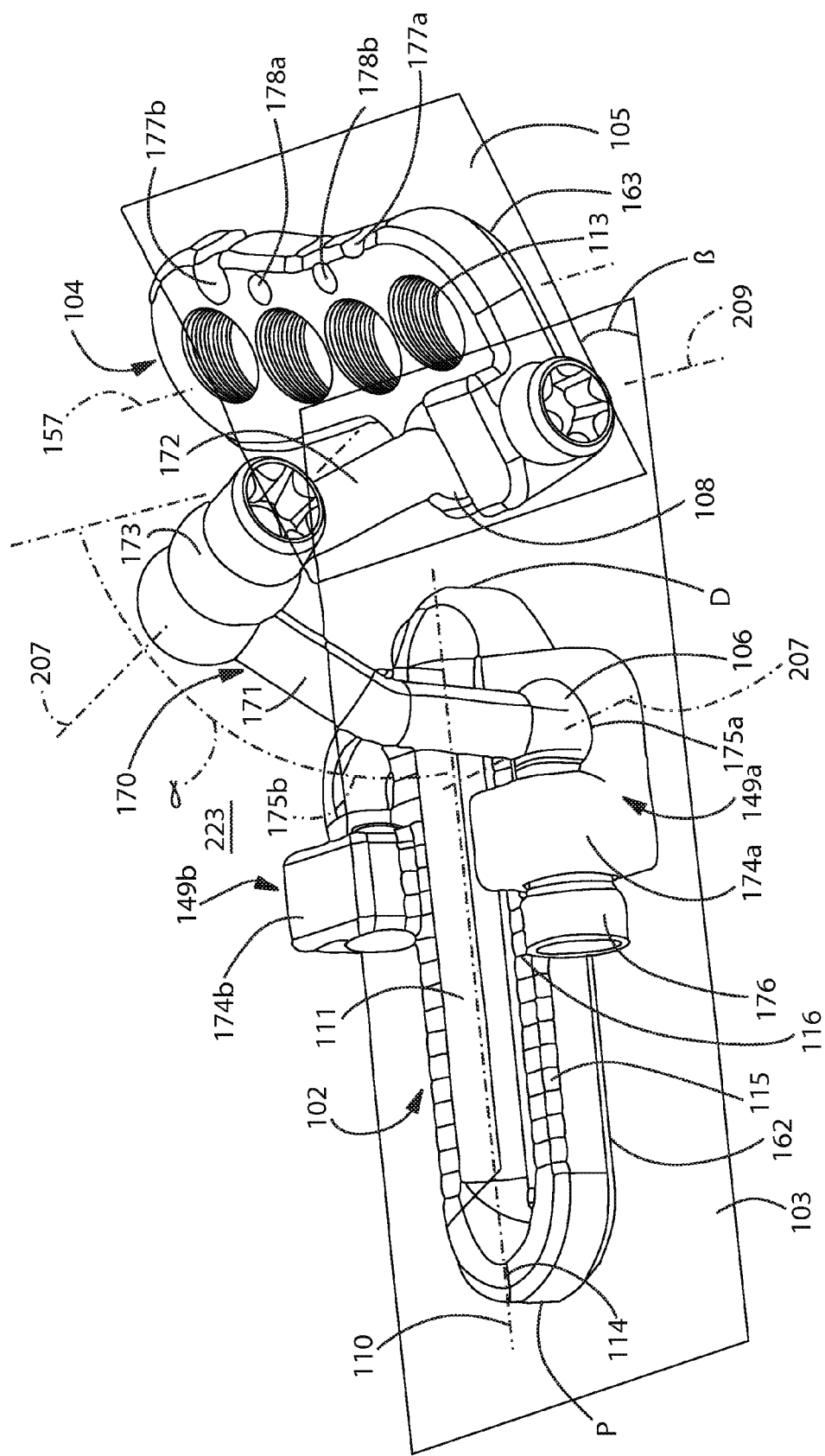
FIG. 10 is a perspective view of a drill guide constructed in accordance with another embodiment.

The configuration of the four plate holes 13; 113 as illustrated in FIGS. 2 and 4 can be applied to each of the embodiments of the drill guide 1; 101 according to FIGS. 1 and 10, respectively. Throughout the disclosure, reference numerals separated by a semicolon refer to embodiments illustrated in FIGS. 1 and 10, respectively, meaning that the description can apply equally to the embodiments of FIGS. 1 and 10). At least one up to all of the four plate holes 13; 113 in the second bone plate 4; 104 can be substantially key-hole shaped. As illustrated in FIG. 2, at least one up to all of the plate holes 13; 113 in the second bone plate 4; 104 can be a combination of two circular holes wherein one of the two circular holes comprises a conical interior thread and the other one is configured as a cylindrical hole with a greater hole diameter forming an enlarged portion 17; 117 of the plate hole 4; 104. The enlarged portion 17; 117 has a hole diameter suitable to allow the head of a bone anchor (e.g., a fixation screw) to pass through. As illustrated in FIG. 2 the enlarged portion 17; 117 of the key-hole shaped plate holes 13; 113 can be laterally arranged so that once the bone anchor is loosened the second bone plate 4; 104 can be laterally displaced until the screw head of the bone anchor coincides with the enlarged portion 17; 117 so that the drill guide 1; 101 can then be removed from the bone without removing the bone anchor. The latter can then be used as a bone anchor for fixing the subsequently inserted bone fixation plate. Instead of arranging the enlarged portion 17; 117 of the key-hole shaped plate holes 13; 113 in a lateral position the enlarged portion 17; 117 can be positioned in a distal position as schematically illustrated in FIG. 4.

Figure 7:
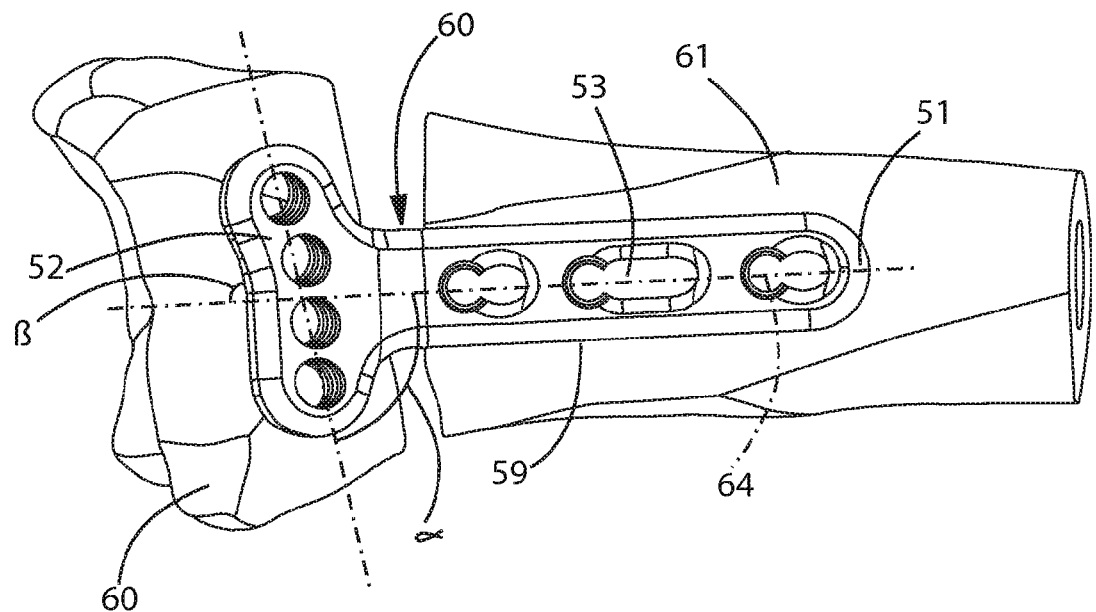
FIG. 7 is a top plan view of a distal radius illustrated in FIG. 6, after the corrective osteotomy has been performed and a T-shaped distal radius bone plate has been positioned on the distal radius.
Figure 8:
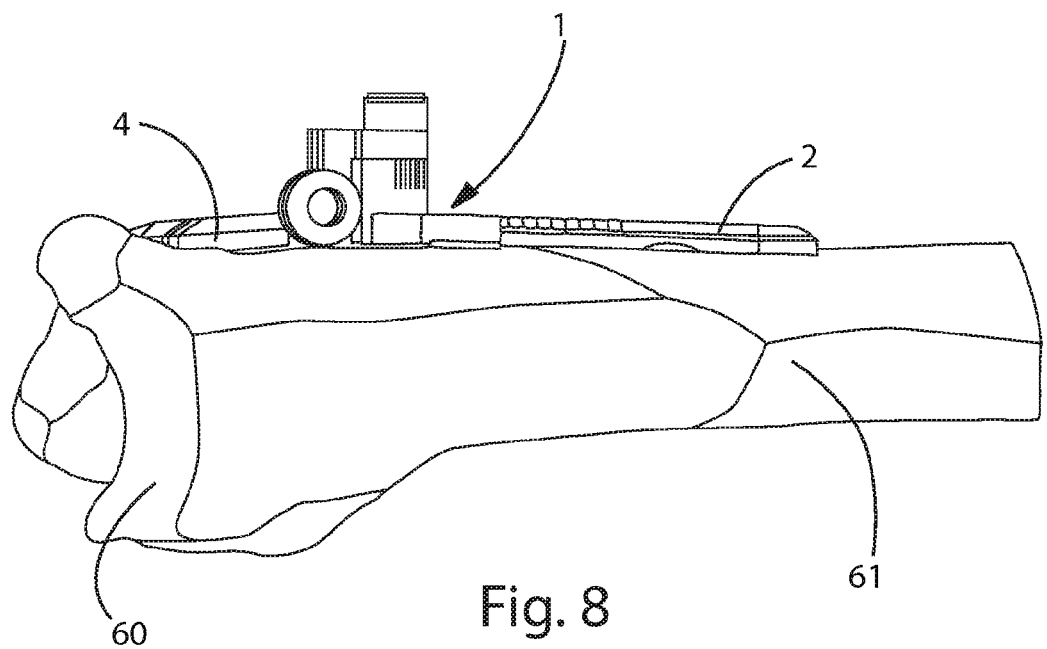
FIG. 8 is a side elevation view of the drill guide illustrated in FIG. 6, positioned on the distal radius prior to performing the corrective osteotomy on the distal radius.
Figure 9:
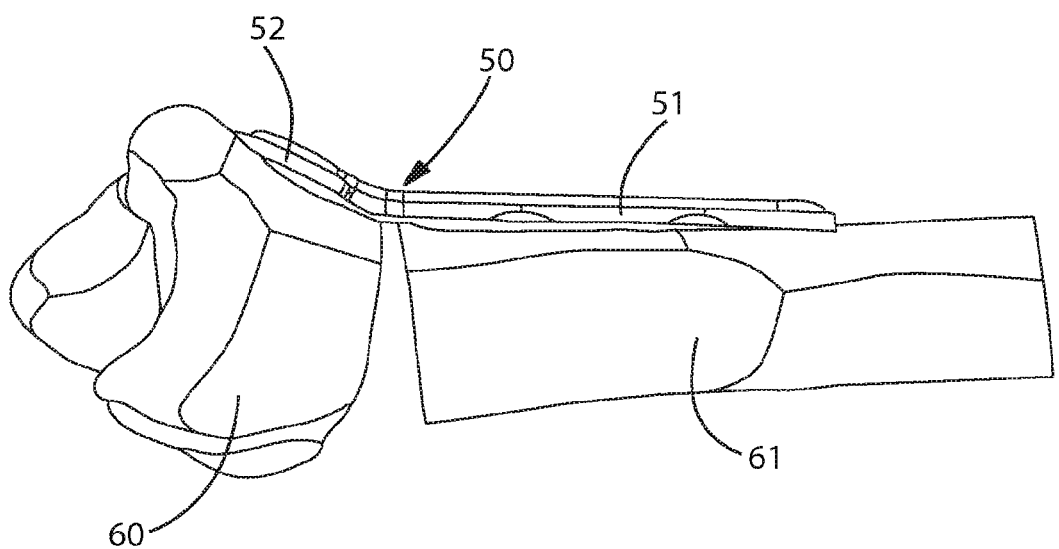
FIG. 9 is a side elevation view of the distal radius as illustrated in FIG. 7, after the corrective osteotomy has been performed and the T-shaped distal radius bone plate has been positioned on the distal radius.

It should be appreciated that the plate holes 13; 113 can be alternatively configured so as to allow the bone plate 4 to be removed from an underlying the bone without first removing the bone anchors that extend through the plate holes 13; 113 and into the underlying bone. For instance, referring to FIG. 3, at least one up to all of the plate holes 13; 113 can define a channel 19; 119 that extends from the respective plate hole 13; 113, for instance in a distal direction, to the outer periphery of the second bone plate 4; 104. Alternatively, the channels 19; 119 of the plate holes 13; 113 can extend in a lateral direction from the plate hole 13; 113 to the periphery of the second bone plate 4; 104. The channels 19; 119 allow the second plate to be removed from respective bone anchors along a direction parallel to the second middle plane 5. It should thus be appreciated that the bone anchors extending through the plate holes 13; 113 can fix the second bone plate 4; 104 to the underlying bone, and can subsequently be loosened to facilitate removal of the second bone plate 4; 104 without removing the bone anchors. The bone fixation plate 50 (see FIG. 7) can subsequently be placed in position on the bone plate 4; 104 such that the bone fixation plate can be slid into position with the channels of the plate holes passing the bone anchors. FIG. 7 shows the holes of the bone fixation plate 50 as being circular in shape. However, it should be understood that the holes can be of any shape. In particular, the holes can have any one or combination of the shapes of the holes shown in FIGS. 2-4. In this regard, the bone plate 50 can be easily positioned on the bone using the bone anchors that have been left in position.

Figure 5:
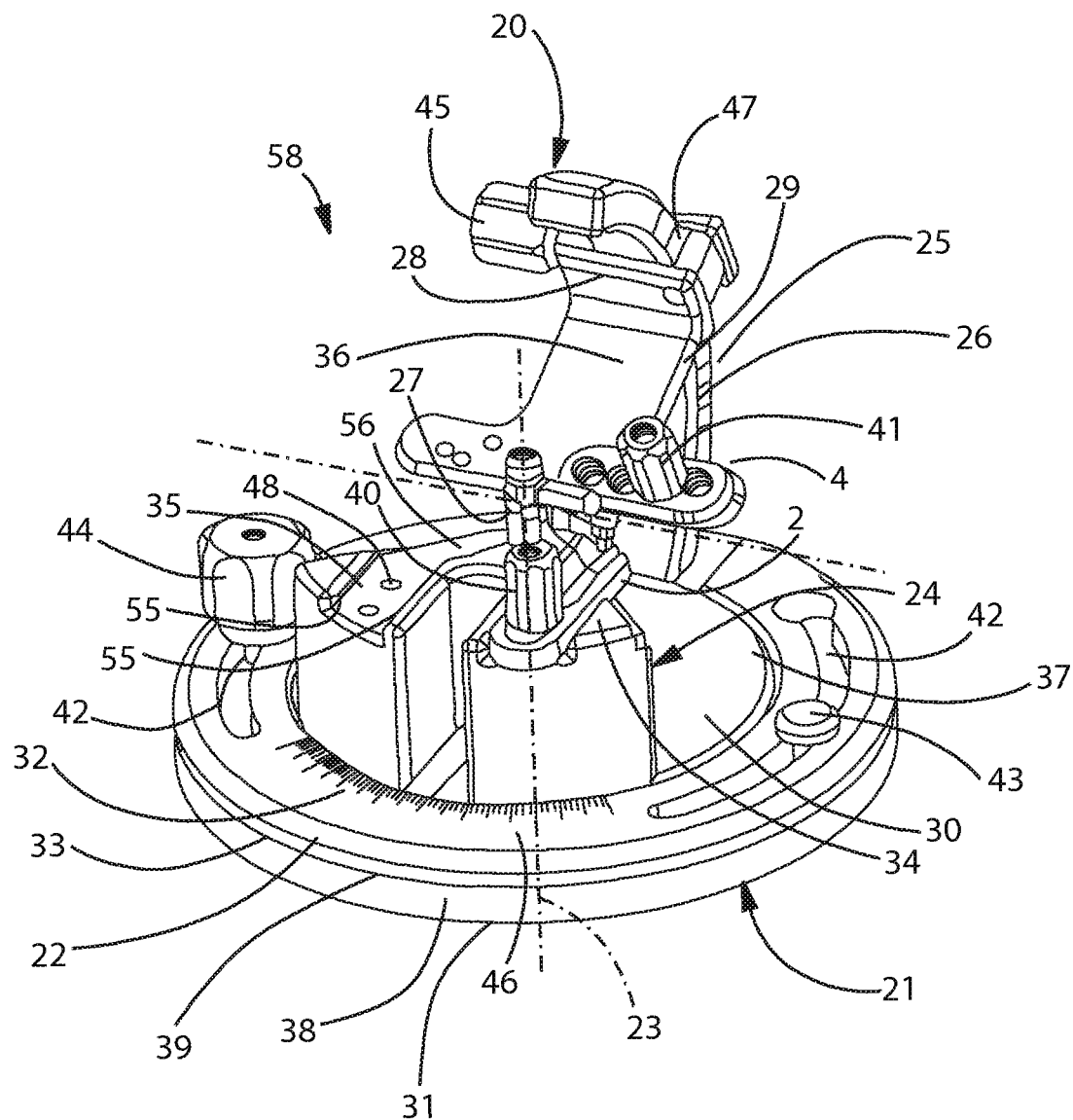
FIG. 5 is a perspective view of a drill guide system including an auxiliary device constructed in accordance with one embodiment for use with the drill guide illustrated in FIG. 1.
Figure 6:
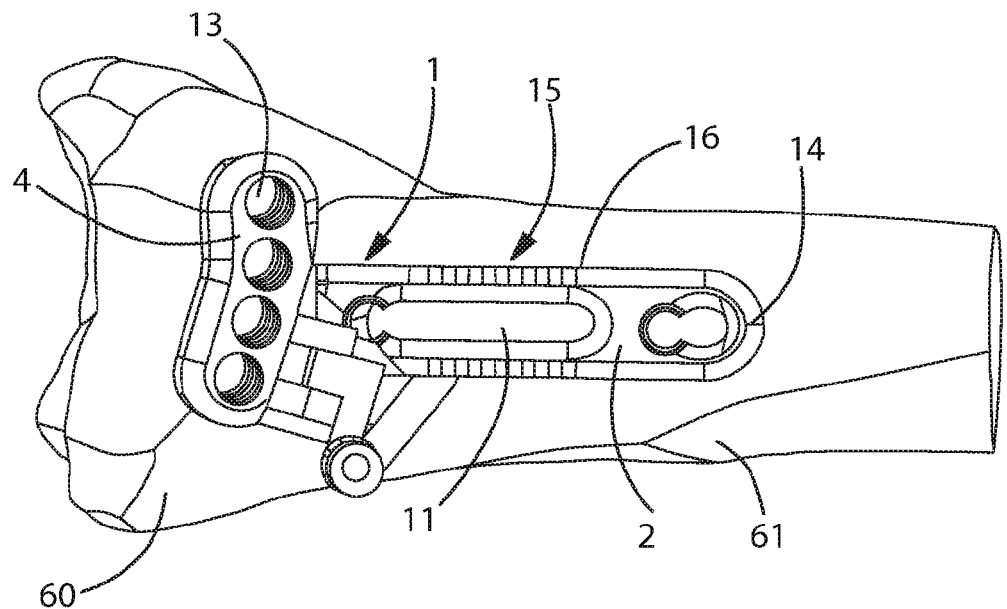
FIG. 6 is a top plan view of the drill guide illustrated in FIG. 1 positioned on a distal radius prior to performing a corrective osteotomy on the distal radius.

Referring now to FIG. 5, a drill guide system 58 includes the drill guide 1 and an auxiliary device 20 configured to adjust at least one or both of the angles α and β to their desired predetermined correction angles. The auxiliary device 20 includes a base plate 21 that defines a central axis of rotation 23, a first positioning member 24 including a first and a second seat 34; 35 configured to receive the drill guide 1 in the right hand configuration or the left hand configuration, a rotatable member 22 supported by the base plate 21 and rotatable relative to the base plate 21 about the central axis 23 so as to adjust the first angle α, and a second positioning member 25 configured to adjust the rotation angle of the second bone plate 4 relative to the first bone plate 2 about the second axis of rotation 9 (e.g., angle β).

The central axis 23 is oriented orthogonal to the first middle plane 3 and coaxial with a circular cylindrical upper portion 37 that defines an upper surface 30, and a lower portion 38 that defines a first sliding surface 39 and an opposed bottom surface 31. The rotatable member 22 can define the shape of a ring that is supported by the base plate 21 in such manner that the bore of the ring is slid over the circular cylindrical upper portion 37 of the base plate 21. The rotatable member 22 has a top surface 32 and an opposed second sliding surface 33 which is slideably arranged on the annular first sliding surface 39 of the base plate 21 so that the rotatable member 22 is rotatable about the central axis 23 of the base plate 21. The rotatable member 22 can be releasably coupled to the base plate.

The rotatable member 22 can be rotated about the central axis 23 of the base plate 21, which causes the second positioning member 25 and the seated second plate 4 to likewise rotate about the central axis 23 relative to the first plate 2, which is supported by the first positioning member 24 at a location independent of the rotation of the rotatable member 22. Alternatively, the first positioning member 24 could be supported by the rotatable member 22 and the second positioning member 25 could be supported independent of the rotatable member (e.g., by the base plate 21). Accordingly, as the rotatable member 22 rotates relative to the first positioning member 24 along an adjustment plane, the first correction angle α is adjusted. A first angular degree scale 46 is located on the top surface 32 of the rotatable member 22 so that the second positioning member 25 can be rotated until the first angle α is substantially equal to the preplanned correction value.

The first positioning member 24 is configured as a block fixedly arranged on the upper surface 30 of the base plate 21 at a location aligned with the axis of rotation 23. The first positioning member 24 can include two seats 34 and 35 that define the adjustment plane orthogonal to the axis of rotation 23 and configured to receive the first bone plate 2 in a position with the first middle plane 3 oriented substantially parallel to the adjustment plane. Each seat 34 and 35 includes two parallel guide walls 55 to laterally position a first bone plate 2 introduced in the respective seat. Each of the two guide walls 55 facing each other comprises an oblique elongation 56 which is directed towards the central axis 23 of the base plate 21. When the drill guide 1 is positioned in the desired seat 34 or 35, the respective oblique elongations 56 abuts the proximal face of the oblique extension 49 of the first bone plate 2. Each of the seats 34 and 35 can further include a retention pin 48 disposed between the guide walls 55. Upon insertion of the first bone plate 2 into one of the seat 34 or 35 the pin 48 passes through the first elongated plate hole 11 in the first bone plate 2 and abuts the proximal end of the first elongated plate hole 11 so that the drill guide 1 is fixedly retained in the seat. The oblique elongation 56 and the pin 48 extending into the first bone plate 2 causes the first bone plate 2 to be retained in the respective seat 34 or 35 such that the first axis of rotation 7 coinciding with the central axis 23 of the base plate 21. It should thus be appreciated that one of the two seats 34 and 35 is configured to receive the first bone plate 2 in the right hand configuration, such that the axis of rotation 7 of the first articulation 6 is aligned with the central axis of rotation 23, and the other of the two seats 34 and 35 is configured to receive the first bone plate in the left hand configuration, such that the axis of rotation 7 of the first articulation 6 is aligned with the central axis of rotation 23.

The first positioning member 24 includes a first fastener 40 configured to releasably fix the first bone plate 2 of the drill guide 1 in one of the first and second seats 34; 35. The first fastener 40 can be configured as a screw which is threadably connectable to either of the first and second seats 34 and 35. In particular, the shaft of the first fastener 40 passes through the second plate hole 12 of the first bone plate 2 while the screw head rests on the top surface of the first bone plate 12 so that the first bone plate 2 can be fixed in the first or second seat 34; 35.

The second positioning member 25 includes at least a pair of positioning elements that are configured to retain the second bone plate 4 and position the second bone plate 4 in a defined position. For instance, the second positioning member 25 comprises an arc shaped member 26 fixed on the rotatable member 22 orthogonally to the second sliding surface 33 and a slideable member 28. The arc shaped member 26 defines an arc extending substantially radially from the adjustment plane defined by the two seats 34 and 35, and the slideable member 28 is slideably disposed on the arc shaped member 28 so as to be slideable along the arc. The slideable member 28 includes a plate 29 that extends radially from the arc shaped member 26 and is configured to adjust the position of the second bone plate 4 about the second angle β. The plate 29 can define a substantially planar surface 36 that is oriented substantially orthogonal to an edge of the arc shaped member 26 so that the bone facing surface 63 of the second bone plate 4 can be disposed on the planar surface 36. The arc shaped member 26 forms an arc with a radius R that has its center 27 lying on the second axis of rotation 9 when the first bone plate 2 of the drill guide 1 is mounted in the respective one of the two seats 34 and 35.

By sliding the slideable member 28 along the arc defined by the arc shaped member 26 the second correction angle β between the second middle plane 5 of the second bone plate 4 and the first middle plane 3 of the first bone plate 2 can be adjusted. A second angular degree scale 47 can be located adjacent to the arc shaped member 26 so that the slideable member 28 can be adjusted until the second angle β is substantially equal to the second angular correction value. The second angle β can be selected so as to allow the second bone plate 4 to rotate about an axis which is orthogonal to the dorsal-palmar direction of the radius and further orthogonal or oblique to the longitudinal axis of the radius after the osteotomy has been performed. The planar surface 36 of the slideable member 28 can define a zero position such that that the angle β defined by the second middle plane 5 and the first middle plane 3 is approximately 25°. Typically the second bone plate 4 is rotated about the second and/or first axis of rotation with an angle in a range between −50° and +40° (for an application for the tibia up to 90°) with respect to the zero position. It should be appreciated that once the first and second angles α and β have achieved their predetermined correction values, the first and second articulations 6 and 8, respectively, can be locked in position to retain the bone plates 2 and 4 in their desired relative position.

The slideable member 28 comprises a second fastener 41 that is configured to releasably fix the second bone plate 4 to the second positioning member 25. The second fastener 41 can be configured as a screw which can be threadably connected to the plate 29 in such manner that the second bone plate 4 is fixed to the plate 29 of the slideable member 28 with its bone facing surface 63 abutting the planar surface 36 of the plate 29. A third fastener 45 is threadably connected to the slideable member 28 in such manner that the tip of the third fastener 45 presses laterally against the arc shaped member 26 when the third fastener 45 is tightened.

The rotatable member 22 further comprises two arc-shaped slots 42. A retaining screw 43 is threadably fixed to the base plate 21 so that its shaft penetrates through one of slots 42 and its head is arranged slightly over the top surface 32 of the rotatable member 22 to axially retain the rotatable member 22 in position relative to the base plate 21. A fourth fastener 44 penetrates through the other slot 42 and is threadably connected to the base plate 21 in order to releasably fix the rotatable member 22 relative to the base plate 21 against rotation about the central axis 23 of the base plate 21. When the fourth fastener 44 is loosened the rotatable member 22 can be rotatably adjusted but is axially kept in position with the retaining screw 43.

Referring now to FIGS. 6-9, a method is illustrated for performing a corrective operation of a malunited fracture of an underlying bone, such as a distal radius. In particular, correction values are pre-operatively planned for aligning two bone segments of the underlying bone that will be created from the underlying bone during an osteotomy procedure. The underlying bone can be a distal radius, and the bone segments can be a radius head 60 and a radius shaft 61 of the distal radius. The correction values can be obtained using two dimensional image data and/or three-dimensional Computer Tomography (CT) data, or the like. The pre-operative planning can include a determination of both angular and length (or translational) correction values based on a previously determined ostoetomy cut line and a select bone fixation plate 50 sized and shaped in a manner consistent with the planned osteotomy, such that the bone fixation plate 50 can retain the bone segments in their desired angular and translational positions. The angular and length correction values can include rotation angles of the osteotomied radius head 60 relative to the radius shaft 61, and a displacement length of the osteotomied radius head 60 relative to the radius shaft 61;

The second bone plate 4; 104 of the drill guide 1; 01 can be adjusted relative to the first bone plate 2; 102 of the drill guide 1; 101 according to a first angular correction value using the auxiliary device 20 in the manner described above. The first angular correction value can correspond to an angle of rotation of the osteotomied radius head 60 about an axis of rotation extending in the dorsal-palmar direction of the radius (see FIG. 6). The second bone plate 4; 104 of the drill guide 1; 101 can be further adjusted relative to the first bone plate 2; 102 to the second angular correction value using the auxiliary device 20 in the manner described above. The second angular correction value can correspond to an angle of rotation of the osteotomied radius head 60 about an axis of rotation extending orthogonal to the dorsal-palmar direction and transverse to the longitudinal axis of the radius (see FIG. 8).

The selected bone fixation plate 50 can be placed over the underlying bone, and the position of the proximal end of the longitudinal portion of the bone fixation plate 50 to be fastened to the radius shaft 61 can be marked on the surface of the radius shaft 61.

The drill guide 1; 101 can then be positioned on the underlying bone with the guiding mark 14; 114 at the free end of the first bone plate 2; 102 of the adjusted drill guide 1; 101 at the position marked under the previous step on the radius shaft 61 by the proximal end of the longitudinal portion of the bone fixation plate 50. The first bone plate 2; 102 of the drill guide 1 can be held in place on the underlying bone manually or by using any suitable instrument.

Next, a first set of bone fixation holes (e.g., at least one such as two holes) can be drilled through the plate holes 13; 113 of the transverse second bone plate 4; 104 of the drill guide 1; 101 into the underlying bone, and in particular into the distal bone segment, or the radius head 60. After the first set of bone fixation holes have been drilled into the radius head 60, the transverse bone plate 4; 104 can be fixed to the radius head 60 with bone anchors.

A second set of bone fixation holes (e.g., at lest one such as two holes) can be drilled through the elongated plate hole 11; 111 that are spaced from the first set of bone fixation holes so as to coincide with the longitudinal correction of the osteotomy. In particular, the drill bits are positioned so as to drill the second set of bone fixation holes at a select location of the scale 15; 115 along the elongated plate hole 11; 111. The location of the scale 15; 115 is spaced a predetermined distance from the zero-position 16; 116 of the scale 15; 115. The predetermined distance coincides with the longitudinal correction value of the osteotomy. It should be further appreciated that the first and second sets of bone fixation holes are positioned so as to define the first and second angular correction values.

Once the first and second sets of bone fixation holes have been created in the underlying bone, the drill guide 1; 101 can be removed from the underlying bone. The transverse bone plate 4 can be removed from the radius head 60 by loosening the bone anchors that extend through the plate holes 13; 113, and the transverse portion 4 can be translatably displaced so that the screw heads of the bone anchors pass through the enlarged portion of the key-hole shaped plate holes (see FIGS. 2 and 4) or that the bone anchors pass through the open plate holes towards the periphery of the transverse portion (see FIG. 3).

The pre-planned osteotomy can then be performed to separate the underlying bone into two bone segments, which are illustrated as the distal radius head 60 and the radius shaft 61. It should be appreciated that the first and second sets of holes defined by the drill guide 1; 101 can alternatively align bone segments of any long bone as desired, for which an osteotomy is to be performed. Thus, in accordance with one embodiment, the angular and length correction values include rotation angles of an osteotomied epiphyseal bone portion relative to a remaining long bone portion and a displacement length of the osteotomied epiphyseal bone portion relative to the remaining long bone portion.

Once the osteotomy has divided the underlying bone into the two bone segments, the pre-selected bone fixation plate 50 can be fixed to the underlying bone segments such that the bone segments are positioned relative to each other at the first and second angular corrective values, and further at the translational corrective value. The bone fixation plate 50 includes a longitudinal portion 59 and a transverse portion 52 that extends from a distal end of the longitudinal portion 59. The transverse portion 52 is then fixed to the radius head 60 at the pre-drilled bone fixation holes using bone anchors (see FIGS. 7 and 9). The radius head 60 and the radius shaft 61 are then reduced angularly and axially (translatably) such that the holes of the second set of holes are aligned with first and second holes 53 and 54 that extend through the longitudinal portion 59. At least one bone anchor is then driven through the first hole 53 of the longitudinal portion 59 into a first hole of the second set of holes, and an additional bone anchor is driven through the second hole 54 of the longitudinal portion 59 into a second hole of the second set of holes.

Figure 11:
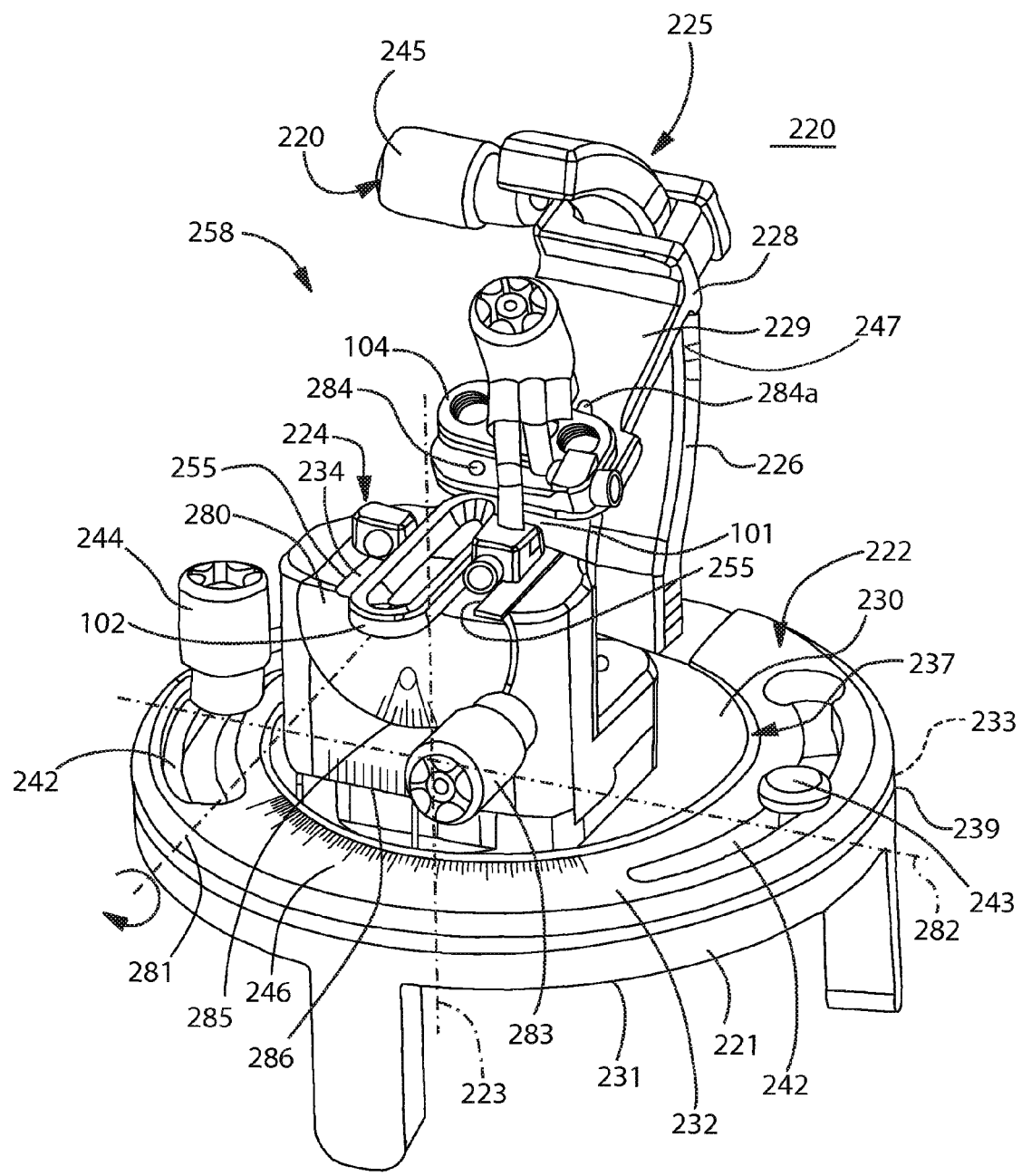
FIG. 11 is a perspective view of a drill guide system including an auxiliary device constructed in accordance with another embodiment for use in combination with the drill guide illustrated in FIG. 10.

The above steps of adjusting the second bone plate 4; 104 of the drill guide 1; 101 relative to the first bone plate 2; 102 can be performed by mounting the drill guide 1; 101 of FIG. 1 or 10 on the auxiliary device 20; 220 of FIG. 5 or 11, respectively, and adjusting the second bone plate 4; 104 relative to the first bone plate 2; 102 by using the first and second positioning members 224; 225 of the auxiliary device 20; 220 and fixing the first and second bone plates 4; 104 and 2; 102 in position. Bone chips can be introduced into the osteotomy gap produced between the two correctly repositioned proximal and distal bone segments 60 and 61 to further facilitate healing.

It should be appreciated that the drill guide system 58 can be provided as a bone fixation kit can be provided for facilitating the drilling of bone fixation holes in bone segments in a pre-operatively planned position. The bone fixation kit of the drill guide system 58 can include one or more drill guides constructed as described herein, and one or more auxiliary devices constructed as described herein. The bone fixation kit of the drill guide system 58 can additionally or alternatively include one or more bone fixation plates as desired, such as a T-shaped bone plate or an L-shaped bone plate in a right side or in a left side configuration, the shape being defined by the transverse and longitudinal portions of the bone plate.

Referring now to FIG. 10, a drill guide 101 constructed in accordance with an alternative embodiment includes a first bone plate 102, a second bone plate 104, a first articulation 106 connected to the first bone plate 102 and a second articulation 108 connected to the second bone plate 104. The first and second articulations 106 and 108 are operably coupled to each other via an articulating arm 170. The first bone plate 102 defines a bone facing surface 162 that extends substantially along a first middle plane 103, and the second bone plate 104 defines a bone facing surface 163 that extends substantially along a second middle plane 105. Each of the first and second articulations 106 and 108 can be configured as a substantially spherical ball-and-socket joint and is releasably lockable using any suitable fastener, such as a set screw 176 that can be tightened against the ball, as desired. The first articulation 106 defines a first center of rotation 207 lying substantially in the first middle plane 103, and the second articulation 108 has a second center of rotation 209 lying substantially in the second middle plane 105. Accordingly, the first and second bone plates 102 and 104 can be moved relative to each other with respect to three degrees of freedom. Each of the first and second bone plates 102; 104 has an elongated shape and the second bone plate 104 is arranged with its long axis transverse to the longitudinal axis 110 of the first bone plate 102. The elongated second bone plate 104 can be slightly angled and comprises a first portion which is fixed at the second articulation 108. The second portion of the second bone 104 extends at an angle relative to the first portion.

The first articulation 106 is coupled to the first bone plate 102 and the second articulation 108 is coupled to the second bone plate 108, and the articulating arm 170 includes first second arm portions 171 and 172 respectively, that are connected between the first and second articulations 106 and 108. The first and second arm portions 171 and 172 are pivotally coupled to each other via a central articulation, which is illustrated as a hinge joint 173.

Furthermore, the first bone plate 102 includes first and second lateral extensions 149a and 149b, respectively. Each extension 149a and 149b includes a respective housing 174a and 174b that defines the respective socket 175a and 175b of one of the ball-and-socket joints. The first and second lateral extensions 149a and 149b can be equidistantly spaced from the longitudinal axis 110 of the first bone plate 102. It should be appreciated that the drill guide 101 can be selectively configured as a guide for the left or right distal radius of a patient by selectively positioning the ball of the first articulation 106 in the desired socket 175a or 175b. The balls of the articulations 106 and 108 can be carried by the free ends of the first and second arm portions 171 and 172, respectively.

The second bone plate 104 can be rotated about the first and/or second centers of rotation 207 and 209, respectively, so as to adjust the first and second angles α and β to their pre-planned correction values. The first bone plate 102 comprises an elongated plate hole 111 that extends substantially extending along the longitudinal axis 110 of the first bone plate 102 as described above with respect to the plate hole 11 of the bone plate 2 (see FIG. 1). The second bone plate 104 comprises at least one such as four plate holes 113 arranged the long axis 157 of the second bone plate 104. Each of the four plate holes 113 can be constructed as described above with respect to the plate holes 13 of the bone plate 2 (see FIG. 1), and thus can include a conical internal thread to receive the screw head of an angularly stable bone anchor.

The first bone plate 102 can include a scale 115 that extends along a direction substantially parallel to the longitudinal axis 110 at a location adjacent the elongated plate hole 111. The scale 115 defines a zero-position 116 which is used to position a drill bit at a distance to the zero-position which corresponds to the pre-operatively planned length correction of the osteotomy. Further, a guiding mark 114 is disposed at the proximal end P of the first bone plate 102 which is suitable to position the drill guide 101 at a marked position on the radius shaft.

The second bone plate 104 can further define a pair of through channels 177a and 177b which are open to a distal periphery of the second bone plate 104 which is located opposite the first bone plate 102. The second bone plate 104 can further define a pair of through holes 178a and 178b, each configured to receive a guide wire.

Referring to FIG. 11, the drill guide system 258 includes the drill guide 101 and an auxiliary device 220 used to adjust the rotation angles between the first and second bone plate 102; 104 of the drill guide 101 in accordance with an alternative embodiment. The auxiliary device 220 includes a base plate 221 that defines a central axis of rotation 223, a rotatable member 222 rotatably supported by the base plate 221 so as to be rotatable relative to the base plate 221 about the central axis 223, a first positioning member 224 including a seat 234 configured to receive a right hand side or left hand side embodiment of the drill guide 101 and a second positioning member 225 configured to adjust the rotation angles α and β, respectively. The axis of rotation 223 can be oriented substantially orthogonal to the first plate plane 3A and coaxial with a circular cylindrical upper portion 237 that defines an upper surface 230, and a lower portion 238 that defines an annular first sliding surface 239 and an opposed bottom surface 231. The rotatable member 222 can be substantially ring shaped and disposed on the base plate 221 such that the bore of the ring is slid over the circular cylindrical upper portion 237 of the base plate 221. The rotatable member 222 defines a top surface 232 and an opposed second sliding surface 233 that is slideably arranged on the annular first sliding surface 239 of the base plate 221 so that the rotatable member 222 is rotatable about the central axis 223.

The rotatable member 222 can be rotated about the central axis 223 of the base plate 221 so as to adjust the first angle α to a value equal to the first correction angle. The auxiliary device 220 further includes a first angular degree scale 246 is located on the top surface 232 of the rotatable member 222 configured to gauge the first angle α as it is adjusted to the first correction angle.

The first positioning member 224 includes a block that is disposed on the upper surface 230 of the circular cylindrical upper portion 237 of the base plate 221. The first positioning member 224 includes a hinge joint 280 that defines an axis of rotation 281 substantially orthogonal to the central axis 223. The hinge joint 280 can be releasably fixable by tightening and loosening a fastener 283. The first bone plate 102 can be tilted about its longitudinal axis 110 via the hinge joint 280. The first positioning member 224 is displaceable along an axis 282 that is substantially orthogonal to the axis of rotation 223 and further substantially orthogonal to the axis of rotation 281, such that the displaceability along the axis 282 can be releasably locked. The seat 234 includes two parallel guide walls 255 to laterally position a first bone plate 102 in the seat 234. The auxiliary device 220 further includes a third angular degree scale 285 and a linear scale 286 that are disposed on the front side of the first positioning member 224 so as to measure the angular displacement of the hinge joint 280 and the translational displacement along the axis 282.

The second positioning member 225 includes an arc shaped member 226 with a radius R fixed on the rotatable member 222 orthogonally to the second sliding surface 233 and a slideable member 228. The arc shaped member 226 extends radially outward from the sliding surface 233. The slideable member 228 is disposed on the arc shaped member 226 and is slideable along the arc. Further, the slideable member 228 includes a plate 229 that extends radially from the arc shaped member 226, and is configured to adjust of the second bone plate 104. The plate 229 can define a plane surface substantially orthogonal to an edge of the arc shaped member 226 so that the bone contact surface 163 of the second bone plate 104 can be extend along the plane surface. One of two positioning pins 284a (one visible in FIG. 11) can be inserted into one of the channels 177a and 177b in the second bone plate 104. The auxiliary device 220 includes a third positioning pin 284c that located adjacent to the side of the second bone plate 104 which is opposite to the channels 177a; 177b. The second bone plate 104 can be positioned on the plate 229 of the second positioning member 225 in a defined position.

Alternatively, the plate 229 of the second positioning member 225 can comprise a step or a ridge so that the second bone plate 104 can abut on the step or ridge and can be held in a defined position by the positioning pin 284b inserted into the channel 177b in case of a right side configuration of the drill guide 101 as illustrated in FIG. 11, or can be held in a defined position by the positioning pin 284a inserted into channel 177b in case of a left side configuration of the drill guide 101.

By sliding the slideable member 228 along the arc defined by the arc shaped member 226 the second correction angle β between the second middle plane 105 of the second bone plate 104 and the first middle plane 103 of the first bone plate 102 can be adjusted. A second angular degree scale 247 is located on one lateral side of the arc shaped member 226 so that the slideable member 228 can be adjusted according to the second correction angle β.

The first positioning member 224 can include a first fastener configured to releasably fix the first bone plate 102 of the drill guide 101 in the seat 234. The slideable member 228 can include a second fastener configured to releasably fix the second bone plate 104 to the second positioning member 225. A third fastener 245 is threadably connected to the slideable member 228 in such manner that the tip of the third fastener 245 presses laterally against the arc shaped member 226 when the third fastener 245 is tightened.

The rotatable member 222 further defines a pair of arc-shaped slots 242. A retaining screw 243 is threadably fixed to the base plate 221 so that its shaft penetrates through one of slots 242 and its head is arranged slightly over the top surface 232 of the rotatable member 222 to axially retain the rotatable member 222 in position relative to the base plate 221. A fourth fastener 244 penetrates through the other slot 242 and is threadably connected to the base plate 221 in order to releasably fix the rotatable member 222 relative to the base plate 221 against rotation about the central axis 223 of the base plate 221. When the fourth fastener 244 is loosened the rotatable member 222 can be rotatably adjusted but is axially kept in position by the retaining screw 243.

Accordingly, the first and second bone plates 102 and 104 can be moved relative to each other with respect to six degrees of freedom. Of the six degrees of freedom, two are provided by being able to rotate the second bone plate 104 relative the first bone plate 102 in a first transverse direction and a second perpendicular direction relative to a plane defined by the first bone plate 102. A third degree of freedom is provided by being able to move the second bone plate 104 in a direction which is perpendicular to the plane defined by the first bone plate 102. A fourth and a fifth degree of freedom are provided by the ability to move the first bone plate 102 relative to the plane it defines in transverse direction to give the fourth degree of freedom and longitudinal direction to give the fifth degree of freedom. That is, the first bone plate 102 is movable both parallel, the fourth degree of freedom, and perpendicular, the fifth degree of freedom, relative to a longitudinal axis of the second bone plate 104. In the embodiment shown in FIG. 11, the fifth degree of freedom is provided by moving the first bone plate 102 externally to the auxiliary device 220. However, as the skilled person would understand, in an alternate embodiment the first bone plate 102 could of course be movable on the auxiliary device 220 to provide the fifth degree of freedom by for example providing the ability to move the hinge joint 280 or the first positioning member 224 parallel to the longitudinal axis defined by the first bone plate 102. The sixth degree of freedom is provided by being able to rotate the first bone plate 102 relative to a longitudinal axis of the first bone plate 102, such as the central longitudinal axis. Other or different degrees of freedom are of course possible, as the skilled person would understand.

Although various embodiments have been described in detail, it should be understood that various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, methods and steps described in the specification. As one of ordinary skill in the art will readily appreciate from the present disclosure, processes, machines, manufacture, composition of matter, methods, or steps, presently existing or later to be developed that perform substantially the same function or achieve substantially the same result as the corresponding embodiments described herein may be utilized.

It will be appreciated by those skilled in the art that various modifications and alterations to the embodiments described herein can be made without departing from the broad scope of the appended claims. Some of these have been discussed above and others will be apparent to those skilled in the art.

The invention claimed is:

1. A drill guide comprising:
    a first bone plate and a second bone plate angularly offset with respect to the first bone plate, each of the first and second bone plates defining at least one hole extending therethrough, the at least one hole configured to position a bone fixation hole on the underlying bone
    a first articulation supported by the first bone plate, the first articulation configured to angularly displace the second bone plate with respect to the first bone plate about a first axis of rotation;
    a central articulation coupled to the first articulation, the central articulation configured to angularly displace the second bone plate with respect to the first bone plate; and
    a second articulation supported by the second bone plate, the second articulation coupled to the central articulation and further configured to angularly displace the second bone plate with respect to the first bone plate about a second axis of rotation that is angularly offset with respect to the first axis of rotation.

2. The drill guide according to claim 1, wherein the first articulation comprises the first axis of rotation and the second articulation comprises the second axis of rotation which is angularly offset with respect to the first axis of rotation.

3. The drill guide according to claim 1, wherein the first bone plate extends along a first plane, and the second bone plate extends along a second plane that is angularly offset with respect to the first plane.

4. The drill guide according to claim 3, wherein one of the first axis of rotation and the second axis of rotation is substantially orthogonal to the first plane.

5. The drill guide according to claim 4, wherein the other one of the first and second axis of rotation lies substantially in the second plane.

6. The drill guide according to claim 1, wherein the first and second articulations are configured as ball-and-socket joints and define first and second centers of rotation, respectively.

7. The drill guide according to claim 6, wherein the first bone plate extends along a first plane, and the second bone plate extends along a second plane that is angularly offset with respect to the first plane, wherein one of the first and second centers of rotation lies substantially in the first plane.

8. The drill guide according to claim 7, wherein the other one of the first and second centers of rotation lies substantially in the second plane.

9. The drill guide according to claim 6, wherein the first articulation is coupled to the first bone plate and the second articulation is coupled to the second bone plate, and the drill guide further comprises an arm that is coupled between the first and second articulations, the arm including a first arm portion and a second arm portion that is pivotally coupled to the first arm portion at the central articulation.

10. The drill guide according to claim 6, wherein the first bone plate comprises a first and a second lateral extension each comprising a housing with a socket of one of the ball-and-socket joints.

11. The drill guide according to claim 10, wherein the first bone plate extends along a central axis, and the first and second lateral extensions are equally spaced from the central axis.

12. The drill guide according to claim 10, wherein the first and second arm portions each comprises a ball of one of the ball-and-socket joints and wherein each ball is located at an end of each of the first and second arm portion opposite the central articulation.

13. The drill guide according to claim 1, wherein the first and second axes of rotation define a first angle with respect to each other.

14. The drill guide according to claim 13, wherein the first angle is adjusted by pivoting the second bone plate relative to the first bone plate about the first axis of rotation.

15. The drill guide according to claim 1, wherein the first bone plate extends along a central axis, and the first axis of rotation is spaced from the central axis.

16. The drill guide according to claim 1, wherein the second bone plate comprises at least two plate holes having a channel extending to a periphery of the second bone plate so as to allow the second plate from to be removed from bone anchors extending through the plate holes.

17. The drill guide according to claim 1, wherein the second bone plate comprises at least two plate holes, each including an enlarged portion allowing a screw head of a bone anchor to pass therethrough.

18. The drill guide according to claim 1, wherein the first bone plate comprises a scale oriented substantially parallel to the central axis of the first bone plate, the scale defining a zero-position.

19. The drill guide according to claim 1, wherein the second bone plate comprises two or more through holes, each through hole configured to receive a guide wire.

20. A drill guide comprising:
a first bone plate that is elongate along a longitudinal direction;
a second bone plate that is angularly offset with respect to the first bone plate, each of the first and second bone plates defining at least one hole that extends therethrough, the at least one hole configured to position a bone fixation hole on an underlying bone;
an extension that projects from the first bone plate in a lateral direction that is angularly offset with respect to the longitudinal direction;
a first articulation that is supported by the extension so as to be spaced apart from the first bone plate in the lateral direction, the first articulation configured to angularly displace the second bone plate with respect to the first bone plate about a first axis of rotation; and
a second articulation that is supported by the second bone plate, the second articulation being coupled to the first articulation, the second articulation configured to angularly displace the second bone plate with respect to the first bone plate about a second axis of rotation that is angularly offset with respect to the first axis of rotation.

21. The drill guide according to claim 20, wherein the second articulation is coupled to the second bone plate, such that, the second axis of rotation is angularly displaced with respect to the first bone plate as the second bone plate is angularly displaced with respect to the first bone plate about the first axis of rotation.

22. The drill guide according to claim 20, wherein the first articulation is configured so that the first axis of rotation is perpendicular to the longitudinal and lateral directions.

23. The drill guide according to claim 20, further comprising an arm that is coupled between the first and second articulations, the arm including a first arm portion and a second arm portion that is pivotally coupled to the first arm portion at a central articulation.

24. The drill guide according to claim 20, wherein the first and second articulations are configured as ball-and-socket joints and define first and second centers of rotation, respectively.

* * * * *